US00PP20604P2

(12) United States Plant Patent
Wood

(10) Patent No.: US PP20,604 P2
(45) Date of Patent: Dec. 22, 2009

(54) ***ABELIA* PLANT NAMED 'LYNN'**

(50) Latin Name: *Abelia hybrida*
Varietal Denomination: Lynn

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/284,871

(22) Filed: Sep. 22, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—Wendy C Haas
(74) *Attorney, Agent, or Firm*—C. A. Whealy

(57) ABSTRACT

A new and distinct cultivar of *Abelia* plant named 'Lynn', characterized by its compact, low mounding and outwardly spreading plant habit; freely branching habit; dense and bushy growth habit; red-colored stems; red purple-colored flower buds; large purple and white-colored flowers; and long flowering period.

3 Drawing Sheets

Botanical designation: *Abelia hybrida.*
Cultivar denomination: 'Lynn'.

BACKGROUND OF THE INVENTION

The present invention relates to a new and distinct cultivar of *Abelia*, botanically known as *Abelia hybrida* and hereinafter referred to by the name 'Lynn'.

The new *Abelia* is a product of a planned breeding program conducted by the Inventor in Grand Haven, Mich. The objective of the breeding program was to develop new compact *Abelias* with large attractive flowers and long flowering period.

The new *Abelia* originated from a cross-pollination during the summer of 2003 of *Abelia schumannii* 'Bumblebee', not patented, as the female, or seed parent and *Abelia×grandiflora* 'Little Richard', not patented as the male, or pollen, parent. The new *Abelia* was discovered and selected by the Inventor on Oct. 10, 2003 as a flowering plant within the progeny of the stated cross-pollination in a controlled environment in Grand Haven, Mich.

Asexual reproduction of the new *Abelia* plant by softwood cuttings in a controlled greenhouse environment in Grand Haven, Mich. since the summer of 2005 has shown that the unique features of this new *Abelia* plant are stable and reproduced true to type in successive generations of asexual reproduction.

SUMMARY OF THE INVENTION

Plants of the new *Abelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Lynn'. These characteristics in combination distinguish 'Lynn' as a new and distinct cultivar of *Abelia:*

1. Compact, low mounding and outwardly spreading plant habit.
2. Freely branching habit; dense and bushy growth habit.
3. Red-colored stems.
4. Red purple-colored flower buds.
5. Large purple and white-colored flowers.
6. Long flowering period.

Plants of the new *Abelia* can be compared to plants of the female parent, 'Bumblebee'. Plants of the new *Abelia* differ from plants of 'Bumblebee' in the following characteristics:

1. Plants of the new *Abelia* have stronger root systems than plants of 'Bumblebee'.
2. Plants of the new *Abelia* are more vigorous than plants of 'Bumblebee'.
3. Plants of the new *Abelia* are more freely branching than plants of 'Bumblebee'.
4. Stems of plants of the new *Abelia* are lighter red in color than stems of plants of 'Bumblebee'.
5. Flower buds of plants of the new *Abelia* are red purple in color whereas flower buds of plants of 'Bumblebee' are dark pink in color.
6. Plants of the new *Abelia* have larger flowers than plants of 'Bumblebee'.

Plants of the new *Abelia* can be compared to plants of the male parent, 'Little Richard'. Plants of the new *Abelia* differ from plants of 'Little Richard' in the following characteristics:

1. Plants of the new *Abelia* have stronger rooting systems than plants of 'Little Richard'.
2. Stems of plants of the new *Abelia* are lighter red in color than stems of plants of 'Little Richard'.
3. Flower buds of plants of the new *Abelia* are red purple in color whereas flower buds of plants of 'Little Richard' are white in color.
4. Flowers of plants of the new *Abelia* are purple and white in color whereas flowers of plants of 'Little Richard' are white in color.
5. Plants of the new *Abelia* have larger flowers than plants of 'Little Richard'.

Plants of the new *Abelia* can be compared to plants of the *Abelia hybrida* 'Edward Goucher', not patented. In side-by-side comparisons conducted in Grand Haven, Mich., plants of the new *Abelia* differed from plants of 'Edward Goucher' in the following characteristics:

1. Flower buds of plants of the new *Abelia* were red purple in color whereas flower buds of plants of 'Edward Goucher' were pink in color.
2. Flowers of plants of the new *Abelia* were purple in color whereas flowers of plants of 'Edward Goucher' were red purple in color.
3. Plants of the new *Abelia* had larger flowers than plants of 'Edward Goucher'.

Plants of the new *Abelia* can also be compared to plants of the *Abelia×grandiflora* 'Prostrata', not patented. In side-by-side comparisons conducted in Grand Haven, Mich., plants of the new *Abelia* differed from plants of 'Prostrata' in the following characteristics:

1. Flower buds of plants of the new *Abelia* were red purple in color whereas flower buds of plants of 'Prostrata' were white in color.
2. Flowers of plants of the new *Abelia* were purple in color whereas flowers of plants of 'Prostrata' were white in color.

BRIEF DESCRIPTION OF THE PHOTOGRAPHS

The accompanying colored photographs illustrate the overall appearance of the new *Abelia*, showing the colors as true as it is reasonably possible to obtain in colored reproductions of this type. Colors in the photographs may differ slightly from the color values cited in the detailed botanical description which accurately describe the colors of the new *Abelia*.

The photograph on the first sheet is a side perspective view of a typical plant of 'Lynn' grown in an outdoor nursery.

The photograph on the second sheet is a close-up view of typical flowers of 'Lynn'.

The photograph on the third sheet is close-up view of typical flowers of 'Lynn' (right), 'Bumblebee' (center) and 'Edward Goucher' (left).

DETAILED BOTANICAL DESCRIPTION

The aforementioned photographs and following observations, measurements and values describe plants grown in Grand Haven, Mich. during the summer and autumn in an outdoor nursery and under conditions which closely approximate commercial production. Plants had been growing for 2.5 years when the photographs and the description were taken. In the description, color references are made to The Royal Horticultural Society Colour Chart, 1995 Edition, except where general terms of ordinary dictionary significance are used.

Botanical classification: *Abelia hybrida* 'Lynn'.

Parentage:

*Female, or seed, parent.*—*Abelia schumannii* 'Bumblebee', not patented.

*Male, or pollen, parent.*—*Abelia×grandiflora* 'Little Richard', not patented.

Propagation:

*Type.*—By softwood cuttings.

*Time to initiate roots.*—About 18 days at 27° C.

*Time to produce a rooted young plant.*—About 40 days at 27° C.

*Rooting habit.*—Freely branching; dense.

Plant description:

*Plant form and growth habit.*—Perennial shrub. Compact, low mounding and outwardly spreading plant habit. Vigorous growth habit.

*Branching habit.*—Freely branching habit, dense and bushy growth habit, usually about 572 lateral branches develop per plant.

*Plant height.*—About 40 cm.

*Plant diameter(area of spread).*—About 63 cm.

Lateral branch description:

*Length.*—About 18.3 cm.

*Diameter.*—About 1.5 mm.

*Internode length.*—About 2.3 cm.

*Aspect.*—About 80° from vertical.

*Texture.*—Pubescent.

*Color.*—Close to 181A.

Foliage description:

*Arrangement.*—Opposite, simple.

*Length.*—About 3.1 cm.

*Width.*—About 1 cm.

*Shape.*—Lanceolate to ovate.

*Apex.*—Acute.

*Base.*—Cuneate to obtuse.

*Margin.*—Slightly serrate.

*Texture, upper surface.*—Slightly pubescent.

*Texture, lower surface.*—Smooth, glabrous.

*Venation pattern.*—Pinnate.

*Color.*—Developing leaves, upper surface: Close to 137A. Developing leaves, lower surface: Close to 146B. Fully expanded leaves, upper surface: Close to 137A; venation, close to 137A. Fully expanded leaves, lower surface: Close to 146B; venation, close to 146B.

*Petiole.*—Length: About 3 mm. Diameter: About 1 mm. Texture, upper and lower surfaces: Smooth, glabrous. Color, upper and lower surfaces: Close to 137A.

Flower description:

*Flower appearance/arrangement.*—Single campanulate flowers; solitary or in clusters; terminal and axillary. Freely flowering habit with numerous flowers developing per lateral branch. Flowers drooping.

*Fragrance.*—Slight, pleasant.

*Flower longevity.*—Flowers last for about one week on the plant. Flowers not persistent.

*Natural flowering season.*—Long flowering period, plants typically flower from spring to fall in Michigan.

*Flower diameter.*—About 3.2 cm.

*Flower depth.*—About 3.5 cm.

*Flower bud.*—Length: About 2.5 cm. Diameter: About 1.2 cm. Shape: Oblanceolate. Color: Close to 61A.

*Petals.*—Arrangement/quantity: Single whorl of five fused petals. Lobe length: About 1.2 cm. Lobe width: About 1.7 cm. Shape: Elliptic. Apex: Obtuse. Margin: Entire. Texture, upper surface: Slightly pubescent. Texture, lower surface: Smooth, glabrous. Color: When opening and fully opened, upper surface: Close to 78A to 78C; towards the margins, close to 155D. Color fading to 78D with development. When opening and fully opened, lower surface: Close to 78B to 78C; towards the margins, close to 155D. Color fading to 78D with development.

*Sepals.*—Quantity/arrangement: Two sepals; opposite. Length: About 1 cm. Width: About 7 mm. Shape: Elliptic. Apex: Acute. Base: Cuneate. Margin: Entire.

Texture, upper and lower surfaces: Smooth, glabrous. Color, immature and mature, upper and lower surfaces: Close to 181B.

*Peduncles.*—Length: About 6 mm. Diameter: About 2 mm. Strength: Strong, flexible. Texture: Smooth, glabrous. Angle: Drooping. Color: Close to 143B.

*Reproductive organs.*—Stamens: Anther size: About 1 mm by 2.5 mm. Anther color: Close to 155D. Pollen amount: Scarce. Pollen color: Close to 155D. Pistils: Pistil length: About 1.6 cm. Stigma shape: Round. Stigma color: Close to 155D. Style length: About 1 cm. Style color: Close to 155D.

*Seeds/fruits.*—Seed and fruit development have not been observed on plants of the new *Abelia* plant.

Garden performance: Plants of the new *Abelia* have been observed to have excellent garden performance and to tolerate rain, wind and temperatures ranging from about −20° C. to about 37° C.

Pathogen/pest resistance: Plants of the new *Abelia* have not been shown to be resistant to pathogens and pests common to *Abelia*.

It is claimed:

1. A new and distinct *Abelia* plant named 'Lynn' as illustrated and described.

* * * * *

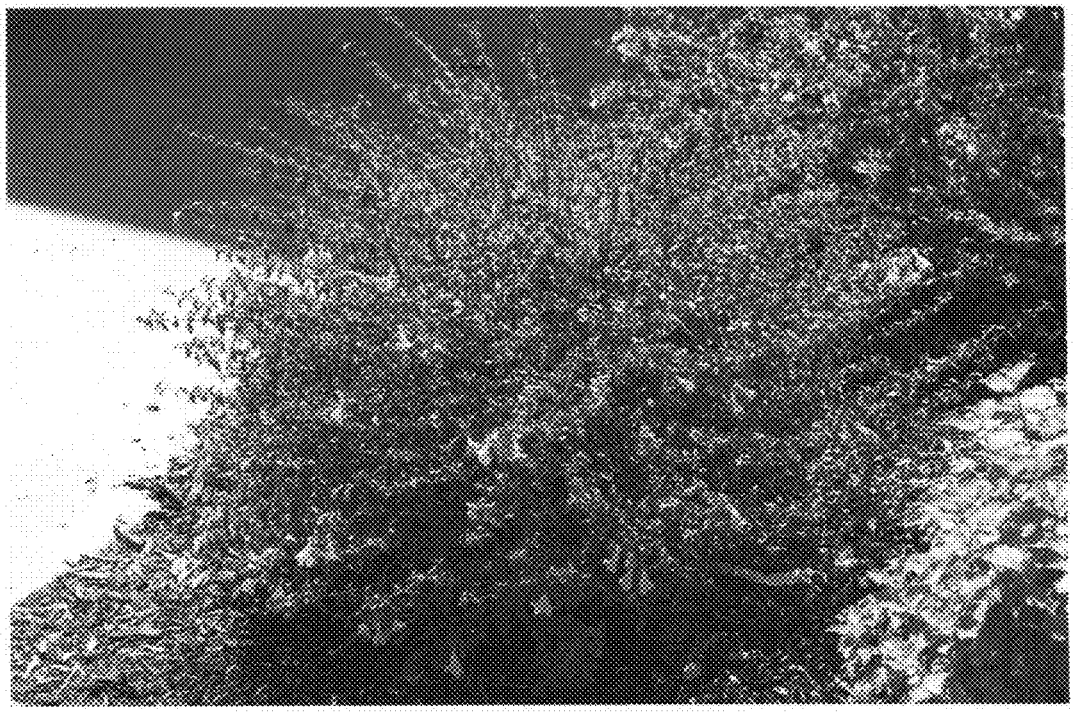

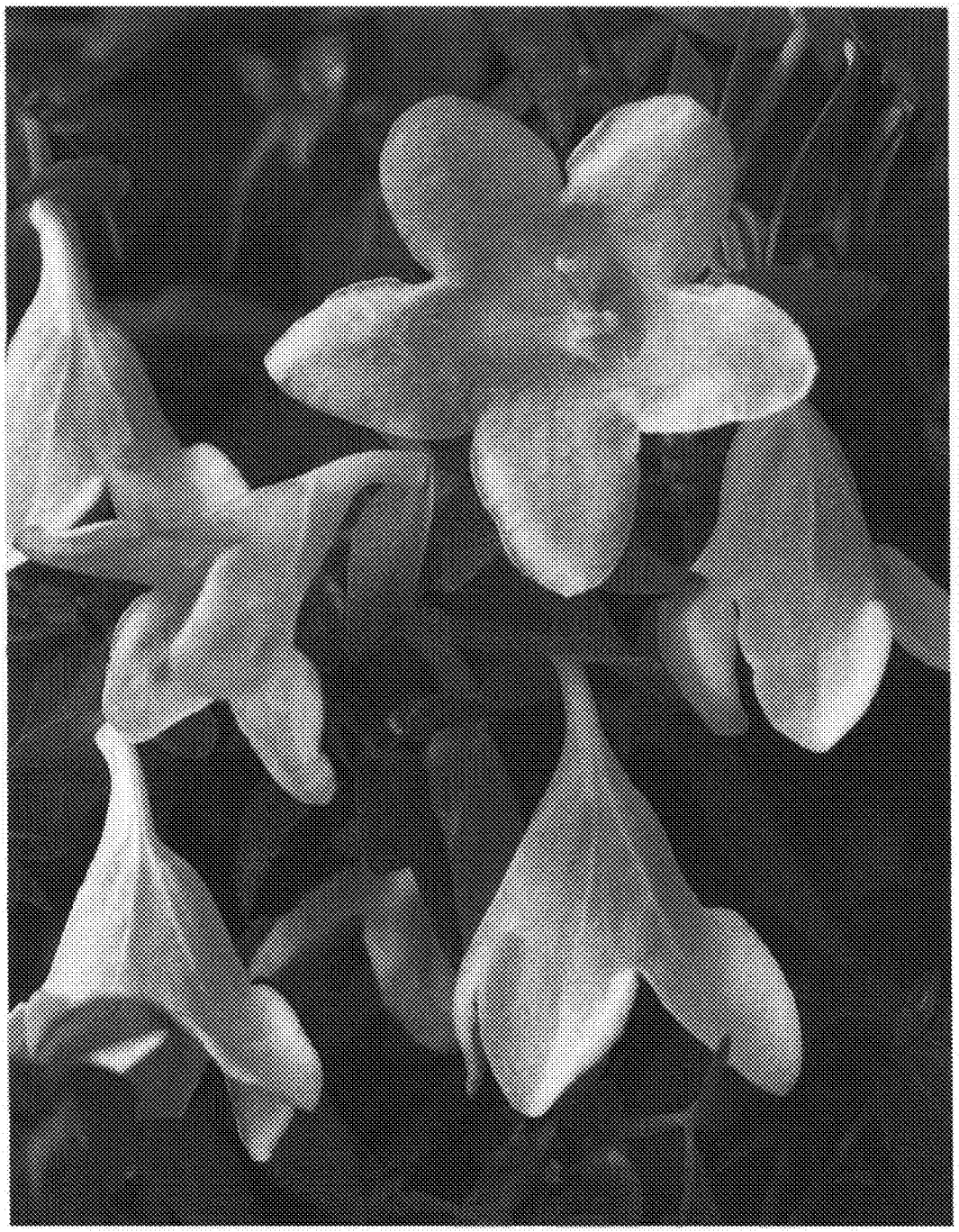

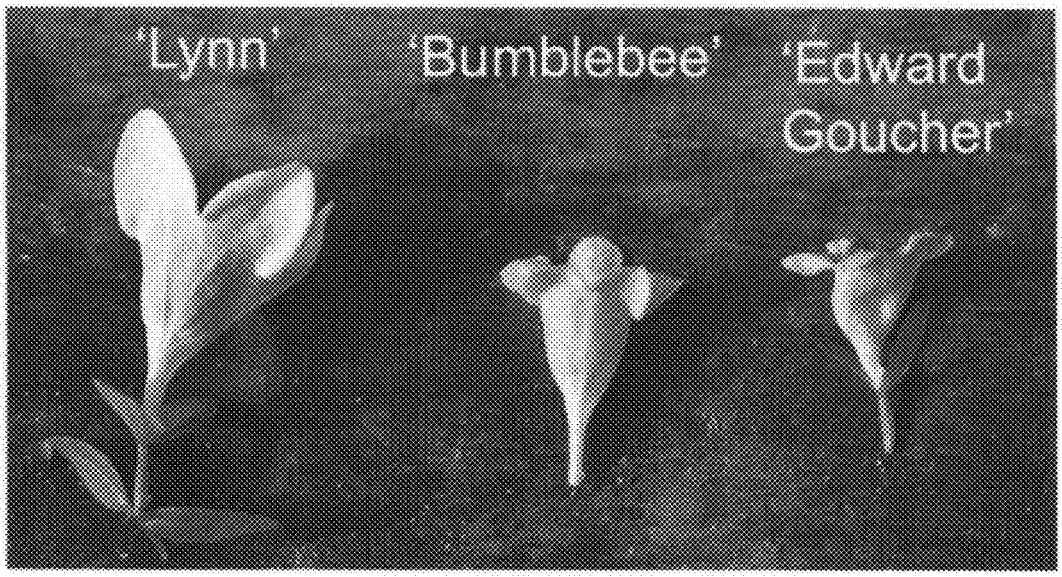
'Lynn'
'Bumblebee'
'Edward Goucher'